United States Patent [19]

Scott et al.

[11] 4,270,725

[45] Jun. 2, 1981

[54] ROLLER CLAMP FOR DEFINING A FLOW LUMEN IN TUBING

[75] Inventors: James W. Scott, Lindenhurst; Joseph A. Bancsi, Vernon Hills, both of Ill.; Jean Kersten, Villers St Amand, Belgium

[73] Assignee: Baxter Travenol Laboratories, Inc., Deerfield, Ill.

[21] Appl. No.: 98,220

[22] Filed: Nov. 27, 1979

[51] Int. Cl.³ .............................................. F16L 55/14
[52] U.S. Cl. .................................................... 251/6
[58] Field of Search ............................................ 251/6

[56] References Cited

U.S. PATENT DOCUMENTS

| | | | |
|---|---|---|---|
| 1,959,074 | 5/1934 | Bloxsom | 251/5 |
| 2,595,511 | 5/1952 | Butler | 251/5 |
| 3,099,429 | 7/1963 | Broman | 251/6 |
| 3,135,259 | 6/1964 | Evans | 128/214 |
| 3,189,038 | 6/1965 | von Pechmann | 137/315 |
| 3,215,395 | 11/1965 | Gorbar | 251/6 |
| 3,297,558 | 1/1967 | Hillquist | 204/195 |
| 3,497,175 | 2/1970 | Koland | 251/9 |
| 3,533,439 | 10/1970 | Hall | 251/6 |
| 3,625,472 | 12/1971 | Rychlik | 251/6 |
| 3,630,481 | 12/1971 | McGay | 251/6 |
| 3,685,787 | 8/1972 | Adelberg | 251/6 |
| 3,802,463 | 4/1974 | Dabney | 251/6 |
| 3,893,468 | 7/1975 | McPhee | 251/6 |
| 3,900,184 | 8/1975 | Burke et al. | 251/6 |
| 3,915,167 | 10/1975 | Waterman | 251/9 |
| 3,918,675 | 11/1975 | Forberg | 251/6 |
| 3,960,149 | 6/1976 | Bujan | 251/6 |
| 4,013,263 | 3/1977 | Adelberg | 251/6 |
| 4,034,773 | 7/1977 | Huggins | 251/9 |
| 4,047,694 | 9/1977 | Adelberg | 251/6 |
| 4,065,093 | 12/1977 | Phillips | 251/6 |
| 4,121,622 | 10/1978 | Forberg | 251/6 |

FOREIGN PATENT DOCUMENTS 1109971 6/1961 Fed. Rep. of Germany .
108209 9/1964 Spain .

OTHER PUBLICATIONS

"How to Use the Travenol Membrane Buretrol ® Set", Publication by Travenol Laboratories, Inc.
"Travenol MP-5 TM Filter System", Publication by Travenol Laboratories, Inc., 1/1975.

Primary Examiner—William R. Cline
Assistant Examiner—H. Jay Spiegel
Attorney, Agent, or Firm—John P. Kirby, Jr.; John A. Caruso; Kirk M. McInerney

[57] ABSTRACT

A two piece roller clamp is disclosed for regulating the fluid flow rate through plastic tubing by defining the size of the tubing lumen. The clamp includes a U-shaped body with a base and two side walls and a longitudinally movable roller mounted in tracks formed in the side walls. The roller is biased against a roller bearing surface running along the length of the base. Adjacent to the roller bearing surface is a tube compression slot having a lower wall uniformly spaced below the roller. A channel of varying cross-section is provided in the lower wall of the tube compression slot. The roller exerts a uniform, but minimal force on the tubing compressing it against the lower wall of the slot permitting the formation of a lumen defined by the contours of the channel. The slot is dimensioned vertically to provide for the minimal compression force by the roller and is dimensioned horizontally to confine the entire compressed cross-section of tubing without excess space thereby conforming the tubing to the contours of the channel to regulate the lumen size. A uniform compression force is maintained during longitudinal movement of the roller by the roller bearing surfaces which prevent perpendicular movement of the roller towards the slot.

7 Claims, 9 Drawing Figures

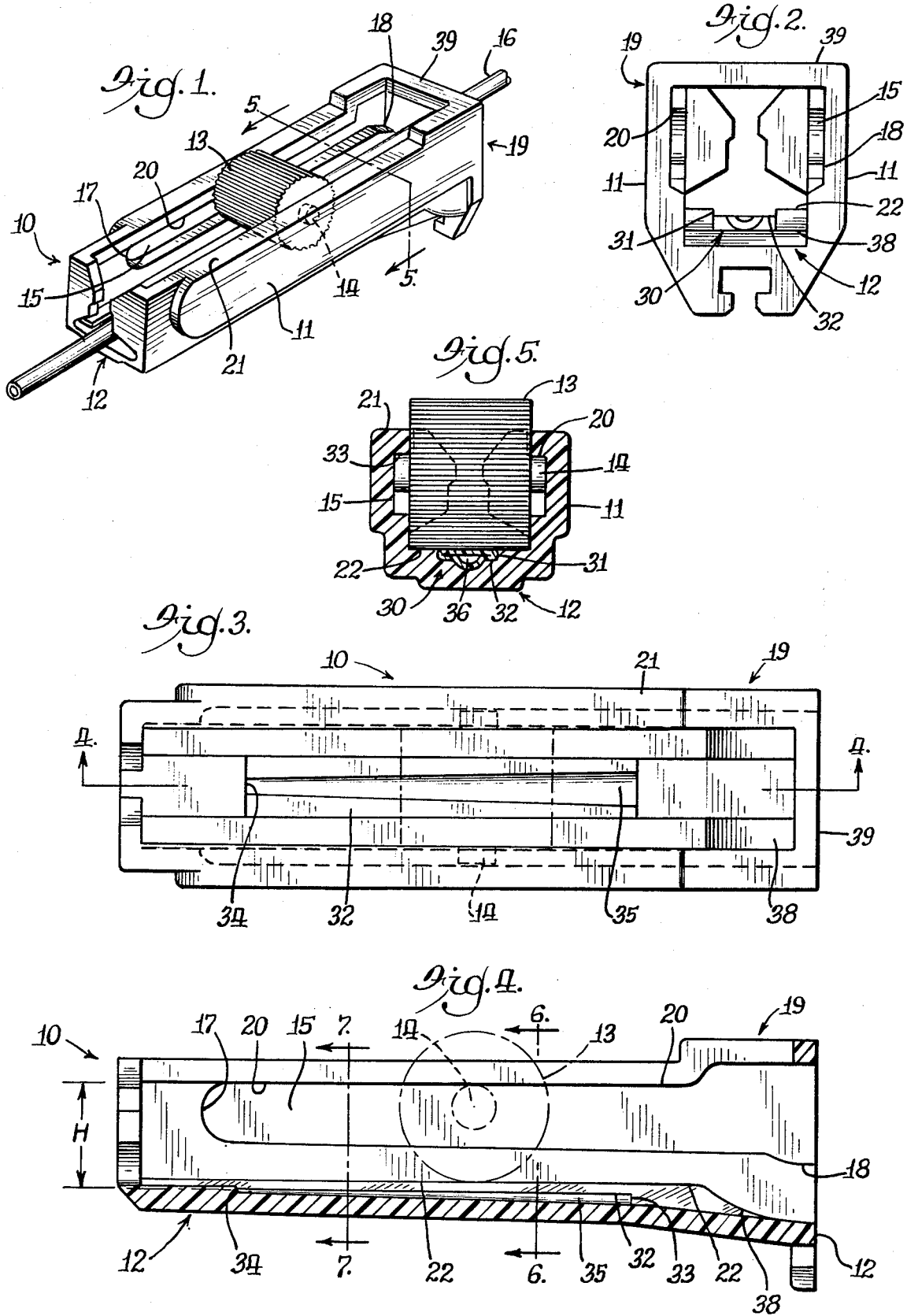

ROLLER CLAMP FOR DEFINING A FLOW LUMEN IN TUBING

BACKGROUND OF THE INVENTION

This invention relates generally to clamps for use with plastic tubing and more specifically to roller clamps for regulating the fluid flow through plastic tubing.

Plastic tubing is extensively employed in parenteral solution administration sets for use in hospitals. Numerous devices such as pinch, screw and roller type clamps have been proposed to regulate the fluid flow rate of the solution reaching the patient by compressing the tubing to vary the size of the tubing lumen. A recurring problem of maintaining a constant flow rate desired for a particular patient has been encountered because of the tendency of the tubing wall to cold flow when compressed under pressure. The phenomena of cold flow produces a migration of the tubing wall causing a progressive change in the cross-sectional areas of the lumen and therefore, the fluid flow rate. Some prior art roller clamps have increased the force of compression against the tube in an attempt to control cold flow. However, this increased force of compression has aggravated the difficulties of cold flow. As a result of the necessity of maintaining an accurate fluid flow rate, frequent monitoring and readjustment of prior roller clamps is required to insure the prescribed flow rate of fluid for the particular patient.

Roller clamps have been proposed to compensate for the phenomena of cold flow by compressing the edges of the tubing against a surface having a centrally disposed channel of varying cross-section to regulate the flow rate by the channel. For example, U.S. Pat. No. 3,685,787 discloses a clamp having a roller spaced above a compression surface to squeeze the opposite edges of the tubing permitting the central portion of the tube to flow into a longitudinal channel in the compression surface to form a lumen. The configuration and cross-sectional area of the channel in that clamp permitted cold flow migration of the compressed tubing wall into the excess channel space causing fluctuations in the desired flow rate. U.S. Pat. Nos. 4,013,263 and 4,047,694 disclose improvements to the embodiment of the U.S. Pat. No. 3,685,787 to direct the cold flow away from the excess space in the channel by providing a series of ridges along the channel to increase the compression on the tubing in an attempt to block cold flow migration into the channel and a recessed roller to permit migration into this additional space. To a certain extent, these improvements tended to direct the cold flow migration of the tubing wall away from the excess space in the channel, but permitted the formation of secondary lumens at the opposite sides of the tubing. As the tubing wall begins to relax causing the cold flow migration, the secondary lumens change size with a corresponding fluctuation in fluid flow rate.

Roller clamps require that the operator apply a manual force to longitudinally move the roller to the desired flow rate setting, both initially and during readjustment of the flow rate to compensate for fluctuations attributable to the phenomena of cold flow. With prior roller clamps, the thumb pressure applied during the manipulation of the roller added to the compressive force on the tubing making it difficult for the operator to effectively adjust the rate setting of those clamps. Specifically, after the operator set the clamp for a desired flow rate by applying thumb pressure to longitudinally position the roller, the flow rate had a tendency to immediately increase slightly. The elimination of the thumb pressure and the corresponding reduction in the compression force of the roller against the tubing caused the size of the lumen to increase producing an undesirable increased fluid flow rate.

Generally, prior roller clamps have been designed to be inexpensive to manufacture of low cost plastic materials in large quantities and are usually disposable. However, it has been difficult to adequately insure manufacturing tolerances within acceptable limits and still maintain low manufacturing costs for prior roller clamp designs. Consequently, problems such as flow rate fluctuations due to cold flow and inability to completely shut off fluid flow were encountered during the use of prior roller clamp designs as a result of the difficulties in monitoring quality control during manufacturing.

OBJECTS OF THE INVENTION

An object of the present invention is to provide an improved roller clamp for plastic tubing which substantially controls fluctuations in flow rate from a pre-determined setting by alleviating the phenomena of cold flow.

A further object of the present invention is to eliminate fluctuations in flow rate caused by additional compression forces against the tubing during movement of the roller.

Still a further object of the roller clamp of the present invention is to minimally compress the tubing within a confined area to alleviate cold flow and to provide an inexpensive clamp which is easily manufactured within acceptable tolerances.

SUMMARY OF THE INVENTION

The present invention provides an easily manufactured and effective roller clamp for plastic tubing which solves the problems of controlling cold flow and eliminates inaccuracies due to the force of manipulation during the time when the operator is adjusting the clamp to the desired flow rate.

The present invention provides a two piece roller clamp having an elongated U-shaped body having a cylindrical roller mounted in tracks formed in the side walls of the body. The base of the body is provided with a roller bearing surface which is spaced uniformly below the tracks and dimensioned to provide a biased, compression fit between the roller axle snugly engaged against the upper axle bearing surfaces of the tracks. The base is further provided with a tube compression slot defined by a uniformly dimensioned shoulder connecting a lower wall of the slot to the roller bearing surface. The coaction of the roller and the dimensions of the tube compression slot in the base provides a uniform force compressing the tubing against the lower wall as the roller is longitudinally moved along the body. The lower wall of the tube compression slot has a channel of varying cross-sectional area which substantially defines the cross-sectional configuration of the flow lumen formed in the tubing. The flow rate is varied by longitudinal movement of the roller in biased engagement with the roller bearing surfaces which prevent perpendicular movement from the force of manipulation. The roller uniformly compresses the sides of the tubing to crimp and confine the cross section of the tubing within the tube-compression slot and within the contours of the channel. The tube compression slot is dimensioned to provide a minimum amount of compression to effectively crimp the tubing but yet alleviate the phenomena of cold flow.

BRIEF DESCRIPTION OF THE DRAWING

FIG. 1 is a perspective view of an embodiment of the roller clamp of the present invention;

FIG. 2 is a right-end view of FIG. 1;

FIG. 3 is a topview of the embodiment of FIG. 1 with a partial illustration in phantom;

FIG. 4 is a longitudinal sectional view taken along the line 4—4 of FIG. 3;

FIG. 5 is a transverse sectional view of the embodiment shown in FIG. 1 shown in operative association with the constricted cross-sectional configuration of plastic tubing at this setting;

DETAILED DESCRIPTION OF THE PREFERRED EMBODIMENTS

Figure 6:
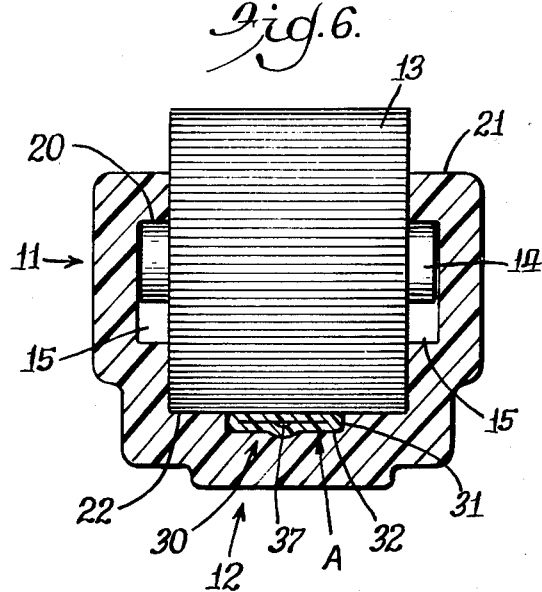
FIGS. 6 and 7 are enlarged transverse views taken along lines 6—6 and 7—7 respectively of FIG. 4 and shown in operative association with the constricted cross-sectional configuration of the plastic tubing at these settings.

Similar reference to characters illustrate corresponding parts and features and referring to FIGS. 1 to 5 there is shown a two-piece roller clamp embodying various aspects of the invention. In the illustrated embodiment of our two-piece roller clamp invention there is included a U-shaped body 10 having upstanding walls 11 which are joined by a base 12. A roller 13 is mounted in longitudinal tracks 15 formed in the side walls 11 by axle hubs 14 centrally disposed on the roller 13. Preferably, the roller 13 has a serrated outer periphery as shown to improve gripping action of a piece of tubing 16. The tracks 15 terminate at one end 17 and are slightly tapered downwardly towards the base 12 at the opposite end 18 into a vertically enlarged portion 19 of the body 10, as shown in FIGS. 1–4. Each track 15 has an axle hub bearing surface 20 which is defined by a perpendicular border 21 slightly projecting horizontally inward into the body 10 and coplanar with one another.

In the orientation of FIG. 4, the base 12 includes a horizontal roller bearing surface or ledges 22 projecting toward the center of the body 10 from both walls 11. The ledges 22 are spaced uniformly below the axle hub bearing surfaces 20 of the tracks 15 along the longitudinal length of the tracks 15 as shown in FIG. 4. The uniform vertical distance H between the hub bearing surfaces 20 and the ledges 22 is slightly less than the distance between the uppermost point 23 on the axle hub 14 and the outer periphery of the roller 13 to create a slightly biased fit, but still permitting longitudinal movement of the roller 13 in the tracks 15. The ledges 22 prevent perpendicular movement of the roller 13 when it is moved longitudinally along the base.

FIGS. 2 and 5 illustrate a tube compression slot shown generally as 30 which is defined by two vertical shoulders 31 connecting the ledges 22 to a lower wall 32 of the slot 30. As shown in FIGS. 4 to 7, the lower wall 32 is uniformly spaced a predetermined distance below the roller bearing ledges 22 along the length of the wall 32. As shown in FIG. 4, the wall 32 begins at a point 33 near the enlarged portion 19 of the body 10; at its opposite end, the wall 32 is stepped slightly upwardly at a point 34 near the end 17 of the roller tracks 15. As shown in FIGS. 3 and 4, a truncated, conical channel 35 is centrally positioned in the lower wall 32 of the tube compression slot 30. The channel 38 decreases progressively in its cross-sectional area from its largest point at the beginning of the lower wall 32 to its truncated end at the point 34 where the lower wall 32 is stepped slightly upwardly.

After the tubing 16 has been connected to a source of administration solution at one end and to the patient by means of a hypodermic needle at its other end, the flow rate is adjusted by longitudinal movement of the roller.

Figure 7:
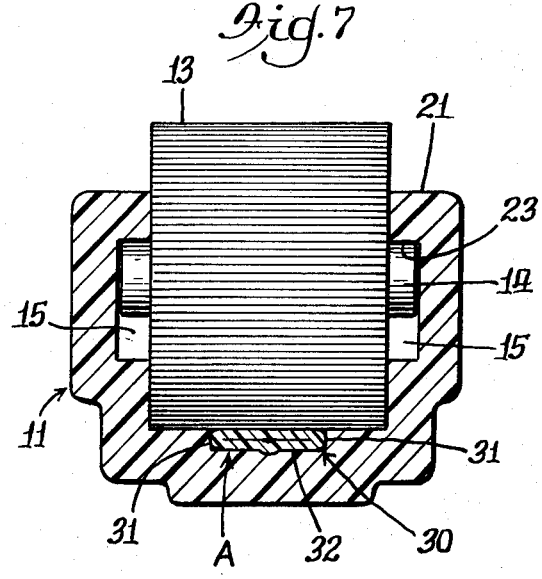

Movement of the roller 13 along the body 10 towards the end 17 of the tracks 15 progressively decreases the size of the fluid passageway or lumen 36 in the compressed tubing from a relatively full flow, open position shown in FIG. 5, to a smaller lumen 37 shown (proportionately enlarged for detail), in FIG. 6 to the point where the flow is completely blocked as shown in FIG. 7. The roller 13 compresses the tubing 16 so that it substantially conforms to the cross-sectional configuration of the tube compression slot 30 directly beneath the roller 13. The opposite sidewalls of the tubing 16 are uniformly compressed by the roller 13 to completely close the sides of the tubing at points A against the lower wall 32. The central portion of the tubing transverse to the compressed sides A conforms to the cross-sectional areas of the channel 35 at the particular position of the roller 13.

The tube compression slot 30 is dimensioned to minimize cold flow by minimizing the perpendicular force exerted by the roller 13 which compresses the tubing 16 against the floor 32. The slot 30 is further dimensioned to confine the size of the lumen to the cross-sectional area of the channel 35 directly beneath the roller 13. The vertical distance between the roller 13 disposed between the ledges 22 and the lower wall 32 is about twice the wall thickness of the tubing 16 or preferably slightly less. This vertical dimension of the shoulders 31 permits the transverse compression force exerted by the roller 13 against the tubing to be minimized, while insuring complete closure of the tubing at points A on either side of the channel 38. This minimized compression force greatly alleviates cold flow migration of the tubing. Correspondingly the tube compression slot 30 is dimensioned to contain the entire cross section of compressed tubing without the need for excess space to accomodate tubing migration. The width of the slot 30 between the shoulders 31 is about equal to the combined dimension of one-half the internal circumference of the tubing bore plus twice the wall thickness of the tubing. The minimized compression force exerted on the tubing between the roller 13 and the lower wall 32 of the tube compression slot 30 enables the tubing to be substantially confined within the contours of the tube compression slot 30 and to assume a lumen configuration defined by the channel 35.

As the position of the roller approaches the step 34 at the truncated end of the channel 35, the size of the lumen will decrease until completely closed at a point just prior to the step 34 as shown in FIG. 7. Complete closure of the tubing lumen normally occurs at a point just prior to the termination of the channel as a result of the vertical distance between the roller 13 and the lower wall 32 of the slot 30 being preferably slightly less than twice the thickness of the tubing wall. Furthermore, manufacturing variations of the tubing wall thickness within accepted tolerances for a particular size tubing might result in complete closure occurring at an earlier point along the length of the clamp for a tubing with a slight excess wall thickness. Alternatively, if the tubing wall is slightly narrower within the manufacturing tolerances, the step 34 will insure complete closure of the tubing lumen, if desired, by appropriately positioning the roller 13.

As described above, the upward biasing force provided by the interference fit between the roller 13 and the ledges 22 insures a uniform transverse compression by eliminating inaccuracies that arise from dimensional variations produced during mass production. Specifically, the vertical distance H as shown in FIG. 4 is dimensioned to insure a snug interference fit of the roller 13 despite slight variations in dimensions between individual mass produced clamps. Consequently, the roller clamp of the present invention may be easily manufactured of inexpensive plastics with an assurance of reliability. Furthermore, the biased fit of the roller 13 against ledges 22 prevents perpendicular movement of the roller 13 against the tubing 16 during manipulation of the clamp. The ledges 22 maintain the uniform compression force against the tubing 16 within the compression slot 30 during adjustment of the clamp.

To permit the insertion of the roller 13 into the body 10, the ledges 22 are tapered downwardly 38 to correspond with the tapered end 18 of the tracks 15 as shown in FIG. 4. As shown in FIGS. 1 and 2, a cross bar 39 horizontally connects the walls 11 at the enlarged portion 19 of the body 10. To assemble the two piece clamp, the tapered ends 18 of the track 15 and the tapered ends 38 of ledges 22 permit the roller 13 to be snapped into place through the enlarged portion 19 and underneath the cross bar 39. Once the hubs 14 of the roller 13 are mounted within the tracks 15, the cross bar 39 prevents removal of the roller 13.

The tubing may be installed either prior to or subsequent to the insertion of the roller 13 into the body 10. If the clamp is assembled in conjunction with a parenteral administration set, oftentimes the tubing is threaded underneath the cross bar 39 and through the clamp body 10 prior to the insertion of the roller 13. On the other hand, where the roller 13 has already been inserted into the clamp body 10, the tubing is inserted underneath the roller 13 which is preferably positioned towards the enlarged portion 19 of the body to make it easier to insert the tubing as a result of the tapered ends 18 and 38.

Figure 8:
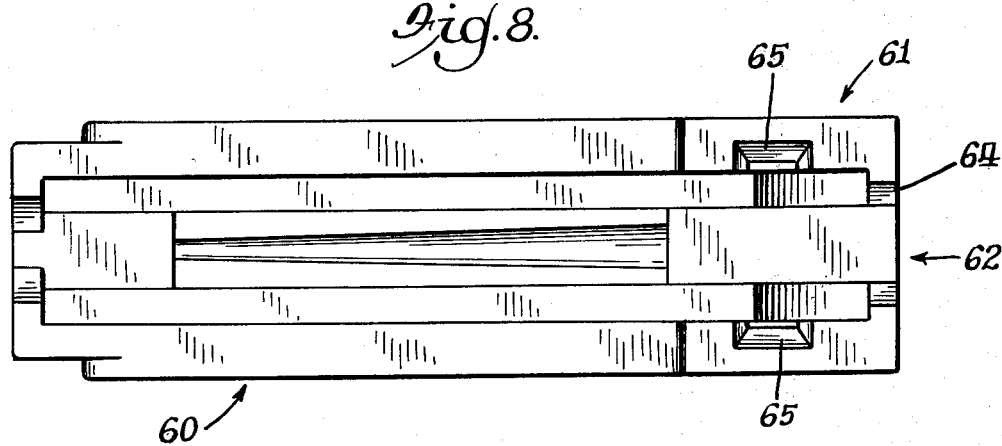
FIG. 8 illustrates another embodiment of the clamp body for the roller clamp of the present invention.
Figure 9:
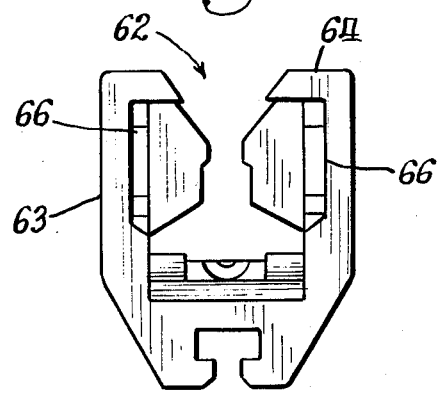
FIG. 9 illustrates a right-end view of FIG. 8.

FIGS. 8 and 9 illustrate another embodiment of the U-shaped body for the clamp of the invention. This U-shaped body 60 is the same as the embodiment previously described with the exception that the cross bar joining the upstanding walls as described above has been eliminated. Specifically, the U-shaped body 60 has an enlarged portion 61 with an opening 62 in place of the cross bar. The opening 62 is defined by the upstanding walls 63 of the body 60. Additionally, each wall 63 has a perpendicular plateau 64 extending slightly into the body 60 defining the opening 62 as shown in FIG. 9. Two tapered slots 65 are provided in the side walls 63 near the enlarged portion 62 of the clamp body 60. The slots 65 are tapered inwardly into tracks 66 to receive the axle hub of the roller (not shown) during assembly of the roller clamp.

The embodiment shown in FIGS. 8 and 9 permits a piece of tubing to be easily inserted into the clamp and the roller conveniently joined with the body 60 by snapping the axle hubs of the roller through the inwardly tapered slots 65. The inward taper of the slots in 66 and a suitable blocking means (not shown) at the end of the tracks 66 nearest the enlarged portion 61 prevents the removal of the roller once the clamp is assembled. With this embodiment, the clamp may be assembled directly to a length of tubing which has couplings at both ends in an assembled parenteral administration set. The opening 62 permits the U-shaped body 60 to be directly fitted over the length of tubing in an assembled administration set.

From the foregoing description of the specific structure of the preferred embodiments, it will be apparent to one skilled in the art that numerous modifications may be made without departing from the spirit of the invention, nor from the scope of the appended claims. All such modifications and alterations are intended to be included within the scope of the invention as defined by the appended claims.

What is claimed is:

1. In a roller clamp for controlling fluid flow through flexible tubing, the clamp having an elongated U-shaped body with rigid opposite upstanding walls joined by a base, a cylindrical roller having an axle mounted at its opposite ends in tracks formed in the walls, the tracks having axle bearing surfaces extending coplanar with one another and parallel to said base, the improvement comprising:

a roller bearing surface in said base spaced uniformly below the axle bearing surfaces of the track a distance to obtain a biased fit between the roller and roller bearing surface by the axle snugly engaging the axle bearing surface on the body to substantially prevent movement of the roller perpendicular to said base and to permit only longitudinal movement of the roller upon application of a manual force to the roller in a direction along the body;

surfaces forming a tube-compression slot in said base including a lower wall spaced uniformly below the level of said roller bearing surface along the body, the tube-compression slot having at least one shoulder joining the lower wall of the slot to the roller bearing surface;

surfaces forming a channel in the lower wall of the tube-compression slot, the channel receiving a portion of the tubing to form a controlled lumen having a cross-sectional configuration substantially the same as that of the cross-sectional configuration of the channel; and said channel further having a cross-sectional area which varies progressively from one position along the base to another in the direction of said longitudinal movement, thereby enabling adjustment of liquid flow through the lumen of the tubing confined within the tube-compression slot and said channel depending on the position of the roller along the body, from the large flow to no flow, substantially without unintended perpendicular movement of the roller along the body and with minimal change in flow over time at any selected position of the roller.

2. The clamp of claim 1 wherein the tube-compression slot is centrally positioned along said body and has two shoulders joining the lower wall of the slot.

3. The clamp of claim 1 wherein the width of the slot is substantially equal to the combined dimension of one-half of the internal circumference of the tubing bore plus twice the wall thickness of the tubing.

4. The clamp of claim 1 wherein the channel has a truncated cone shape.

5. The clamp of claim 1 wherein the shoulder of the tube-compression slot has a height which is slightly less than or equal to twice the wall thickness of the tubing.

6. The clamp of claim 1 wherein the elongated U-shaped body is longitudinally unobstructed along its length opposite to the base to permit sideways insertion of the tubing into the clamp body, prior to assembling the roller with the body.

7. The clamp of claim 1 or 6, further including diametrically opposed slots in the upstanding side walls of the body oriented to receive the axle of the roller during assembly of the roller with the body.

* * * * *